(12) United States Patent
Suzawa et al.

(10) Patent No.: US 6,485,888 B1
(45) Date of Patent: Nov. 26, 2002

(54) FLUORINATED ALCOHOL FOR MANUFACTURING OPTICAL RECORDING MEDIUM AND OPTICAL RECORDING MEDIUM USING THE SAME

(75) Inventors: Kazuki Suzawa, Komoro (JP); Hiroyuki Arioka, Nagano (JP); Tomoki Ushida, Saku (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/627,149

(22) Filed: Jul. 27, 2000

(30) Foreign Application Priority Data

Jul. 28, 1999 (JP) ............................................. 11-214232

(51) Int. Cl.[7] ................................................. G11B 7/24
(52) U.S. Cl. .................. 430/270.15; 430/945; 252/587; 568/842
(58) Field of Search ........................... 430/270.15, 945; 568/842; 252/587

(56) References Cited

U.S. PATENT DOCUMENTS 4,346,250 A * 8/1982 Satokawa et al. ............ 568/842
5,902,698 A * 5/1999 Nie et al. .................... 429/194

FOREIGN PATENT DOCUMENTS

| EP | 0398154 | * | 11/1990 |
| EP | 0967193 | * | 12/1999 |
| EP | 0968990 | * | 1/2000 |
| GB | 2109270 A | | 6/1983 |
| JP | 63159090 A | | 7/1988 |
| JP | 3120635 | | 5/1991 |
| JP | 3219445 | | 9/1991 |
| JP | 04-008585 | * | 1/1992 |
| JP | 07137448 A | | 5/1995 |

OTHER PUBLICATIONS

Peters et al., "Chemical Separations and Measurements", W.B Saunders Co., pp. 472–482,523–544 & 560–573 (1974).*

* cited by examiner

*Primary Examiner*—Martin Angebranndt
(74) *Attorney, Agent, or Firm*—Rader, Fishman & Grauer PLLC

(57) ABSTRACT

The present invention provides a fluorinated alcohol for manufacturing an optical recording medium that is superior in the characteristics and weatherability, and an optical recording medium having an organic dye layer formed by using the fluorinated alcohol.

A fluorinated alcohol for manufacturing an optical recording medium having an organic dye layer and a reflecting layer in this order on a light-transmittable substrate, wherein a content of a high-boiling-point fluorinated alcohol with a boiling point of not less than 120° C. is 0.001% by weight or less. An optical recording medium is provided with an organic dye layer formed by using the ultra-high purity fluorinated alcohol.

6 Claims, No Drawings

FLUORINATED ALCOHOL FOR MANUFACTURING OPTICAL RECORDING MEDIUM AND OPTICAL RECORDING MEDIUM USING THE SAME

BACKGROUND OF THE INVENTION

1. Field of the Invention

The present invention relates to a fluorinated alcohol which, upon manufacturing an optical recording medium having an organic dye layer, is used for forming the organic dye layer, and also concerns an optical recording medium having an organic dye layer formed by using the fluorinated alcohol.

2. Description of the Related Art

That an organic dye such as a cyanine type, phthalocyanine type or azo type is used for recording layers of writable so-called recordable type optical recording media as represented by CD-R and DVD-R has been known.

In general, the formation of such an organic dye recording layer is carried out as follows: To an organic solvent containing, alone or in combination, such as cyclohexane, cyclohexanone, methanol, ethanol, isopropyl alcohol, diacetone alcohol, methyl cellosolve, ethyl cellosolve, butyl acetate or fluorinated alcohol, a dye as aforementioned is added and dissolved to prepare a dye solution, and this dye solution is applied onto a substrate by a spin coating method.

In recent years, fluorinated alcohol has come to be used for a dye-applying solvent, and many patent applications have been filed concerning this technique. For example, Japanese Examined Patent Publication No. 7-96333/1995 discloses the use of fluorinated alcohol. Japanese Laid-Open Patent Publication No. 4-8585/1992 discloses the use of fluorinated alcohol having a purity of not less than 99% by weight. Moreover, Japanese Laid-Open Patent Publication No. 7-137448/1995 discloses the use of 2,2,3,3-tetrafluoro-1-pronanol having a pH of not less than 6.0.

SUMMARY OF THE INVENTION

Here, an optical recording medium needs to have superior weatherability by taking into consideration various working environments. Thus, it is a prerequisite for a solvent for dissolving an organic dye not to give adverse effects to the weatherability of the optical recording medium.

The inventors of the present invention have studied extensively about the weatherability required for the optical recording medium, and have found that, among optical recording media manufactured by using fluorinated alcohol as an organic dye applying solvent, some of them are inferior in the characteristics and weatherability, as compared with the other media.

In general, fluorinated alcohol has been known as aliphatic alcohol containing fluorine atoms, and represented by a general formula: A—$CH_2OH$ (where A represents $CF_3$ or $H(CF_2\text{-}CF_2)n$, and n is a positive integer), and among these, those having a molecular weight in the range of 132 to 332 (n=1 to 3) and a boiling point in the range of 109 to 170° C. have been well known.

As a result of further researches, it has been found that those optical recording media that are inferior in the weatherability have further degradation in the characteristics and weatherability, when the fluorinated alcohol to be used contains a high-boiling-point fluorinated alcohol with a boiling point of not less than 120° C. in an amount of not less than a certain amount, when the high-boiling-point fluorinated alcohol has a molecular weight in the range of 150 to 500, and when the high-boiling-point fluorinated alcohol is fluorinated alcohol represented by a general formula: A—$CH_2OH$, where A represents $H(CF_2—CF_2)n$ and n is in the range of 2 to 4. Here, even in the case when the fluorinated alcohol to be used contains such a high-boiling-point fluoric alcohol, if the content thereof is 0.001% by weight or less, the resulting optical recording medium are superior in the characteristics and weatherability.

An object of the present invention is to provide an ultra-high purity fluorinated alcohol for manufacturing an optical recording medium that is superior in the characteristics and weatherability. Moreover, another object of the present invention is to provide an optical recording medium that is superior in the characteristics and weatherability and that has an organic dye layer formed by using the ultra-high purity fluorinated alcohol.

The present invention is a fluorinated alcohol for manufacturing an optical recording medium having an organic dye layer and a reflecting layer in this order on a light-transmittable substrate, wherein a content of a high-boiling-point fluorinated alcohol with a boiling point of not less than 120° C. is 0.001% by weight or less.

The molecular weight of the high-boiling-point fluorinated alcohol is, for example, 150 to 500. Moreover, the high-boiling-point fluorinated alcohol is mainly represented by, for example, general formula (1):

$$H(CF_2—CF_2)n—CH_2OH \qquad (1)$$

(where n is an integer of 2 to 4).

The present invention is an optical recording medium having an organic dye layer and a reflecting layer in this order on a light-transmittable substrate, wherein said organic dye layer is formed by using a solvent containing a fluorinated alcohol in which a content of a high-boiling-point fluorinated alcohol with a boiling point of not less than 120° C. is 0.001% by weight or less.

In accordance with the present invention, an ultra-high purity fluorinated alcohol in which the content of a high-boiling-point fluorinated alcohol with a boiling point of not less than 120° C. is 0.001% by weight or less is used as a manufacturing solvent of an optical recording medium having an organic dye layer. Therefore, it is possible to provide an optical recording medium that is superior in the electric characteristics and reliability.

DETAILED DESCRIPTION OF THE INVENTION

The structure of the optical recording medium of the present invention is fundamentally the same as those of current Recordable type optical recording media. In the structure, an organic dye recording layer which serves to record and reproduce using laser light is formed on a light-transmittable substrate formed with a pregroove, a reflecting layer increasing light-reflectance is formed on the organic dye recording layer and further a protective layer which protects the organic dye recording layer and the reflecting layer is formed on the reflecting layer.

An optical recording medium obtained by using the optical recording medium having such a layer structure as at least one party and by laminating it to the other through an adhesive layer is also included in the present invention. Alternatively, an optical recording medium in which the adhesive layer doubles as a protective layer on the reflective layer is also included in the present invention. Further, in order to arise the scuff resistance of the light-transmittable substrate, an organic protective layer may be formed on the opposite surface of the substrate with respect to the organic dye layer.

As materials of the light-transmittable substrate, for example, a polymer material typified by a polycarbonate resin, acrylic resin, polystyrene resin, epoxy resin, polyester resin, vinyl chloride resin or polyolefin resin or an inorganic material such as glass may be used. A pregroove of stamper is transferred by primarily injection molding in the case of using a resin material and by primarily a 2P method in the case of using glass, thereby preparing the substrate.

Then, the organic dye layer including an organic dye as its major component is formed on the substrate.

The organic dye layer may be any one of those which can read a variation, in shape or optical properties, which is made due to a physical and/or chemical change caused by the absorption of recording laser light, by using reproducing laser light. For the formation of a locally denatured portion, for instance, a phthalocyanine dye, cyanine dye or azo dye which has an absorption area in the wavelength range of a semiconductor laser is used very often. These dyes may be used either singly or in combinations of two or more, to which a singlet oxygen quencher, a UV-ray absorber or the like may be added as required. It is also preferable to use an ionic bonding material of a dye cation and an anion of singlet oxygen quencher as the organic dye.

In the present invention, a coating solution is prepared by dissolving an organic dye in an organic solvent and the coating solution is applied onto the substrate by a spin coating method to form the organic dye layer. It is desirable to control the concentration of an organic dye component in the coating solution and the thickness of the organic dye layer to be formed so that sufficient reflectance can be obtained after the reflecting layer is formed.

With respect to the organic solvent used for the preparation of the coating solution, 2,2,3,3-tetrafluoro-1-propanol (TFP) may be used alone as an ultra-high purity fluorinated alcohol, or a solvent other than the fluorinated alcohol may be mixed therewith, if necessary. Here, upon selection of the other solvent to be mixed, it is necessary to select such a solvent that not only dissolves the organic dye, but also gives no adverse effects on the light-transmittable substrate to be used. With respect to the other solvent, examples thereof include: cyclohexane, cyclohexanone, methanol, ethanol, isopropyl alcohol, diacetone alcohol, methyl cellosolve, ethyl cellosolve, butyl acetate, etc. In the case when a solvent other than the fluorinated alcohol is added, the amount thereof is preferably approximately less than 10% by weight with respect to the amount of the fluorinated alcohol.

The main feature of the present invention is that fluorinated alcohol is further distilled up to a purity level where the content of a high-boiling-point fluorinated alcohol having a boiling point of not less than 120° C. and a molecular weight of 150 to 500, and represented by the above-mentioned general formula (1) where n is an integer from 2 to 4, is 0.001% by weight or less, and resulting ultra-high purity fluorinated alcohol is used. The content may be any content as long as it is not more than 0.001% by weight, and may be 0% by weight. Fluorinated alcohol tends to include those having high molecular weights (n=2, 3, 4) due to its inherent manufacturing process. Such an ultra-high purity fluorinated alcohol has not been used in the manufacturing process of an optical recording medium.

As indicated by the relationship between the value of n in the general formula (1) and the molecular weight or the boiling point shown in Table 1, as the value n increases, the boiling point also rises in order; therefore, it is possible to increase the purity through distillation.

TABLE 1

| n* | Molecular weight | Boiling point |
|---|---|---|
| 1 | 132.06 | 109~110 (° C. /760 mmHg) |
| 2 | 232.07 | 140~141 (° C. /760 mmHg) |
| 3 | 332.09 | 169~170 (° C. /760 mmHg) |
| 4 | 432.10 | 155~156 (° C. /200 mmHg) |
| 5 | 532.11 | 180~181 (° C. /200 mmHg) |

Molecular weight and boiling point of general fluorinated alcohol

*n represents the value n in general formula (1): $H(CF_2-CF_2)n-CH_2OH$

The organic dye layer is formed by a spin coating method in the same manner as the conventional process. That is, a dye and, if necessary, singlet oxygen quencher and a binder are dissolved in ultra high-purity fluorinated alcohol to prepare an coating solution, and this solution is applied on a substrate by a spin coating method, and then the coat layer is dried, if necessary. Here, another application method, such as a screen printing method and a dipping method, may be used. The thickness of the organic dye layer is generally in the range of 10 to 500 nm at groove portions, and more preferably, 50 to 300 nm.

A reflecting layer having a thickness of about 10 to 500 nm, made of metal, is directly formed on the organic dye layer. This reflecting layer is formed by using elements, such as Au, Ag, Al, Cu, Cr, Ni, Si and Ge, alone or with another element being contained, through a formation method such as a sputtering method and a vacuum vapor deposition method.

A protective layer with a thickness of, for example, 1 to 50 $\mu$m is formed on the reflecting layer. Layers which can protect the organic dye recording layer and the reflecting layer suffice for the protective layer, and there is no particular limitation to the structural material of the protective layer. As the material of the protective layer, a UV-ray curable type acrylic resin is usually used from, for example, the reason that the protective layer can be formed with ease. The material of the protective layer may also be an organic material such as a vinyl chloride resin, epoxy resin or polyester resin or an inorganic material such as $SiO_2$ or AlN. These materials may be either singly or as a mixture. The protective layer may comprise multiple layers in which different materials are laminated.

On the protective layer, a label printing layer may be further formed.

Moreover, when such an optical recording medium is laminated with an adhesive layer being provided on the side opposite to a plane of incidence of light, the adhesive layer may double as the protective layer.

Preferably the protective layer is formed by a spin coating method in order to avoid damages to the reflecting layer. However, the protective layer may be formed by a screen printing method, dipping method or spray coating method etc.

In the present invention, upon formation of the organic dye layer, ultra high-purity fluorinated alcohol is used so that the resulting optical recording medium has superior characteristics and weatherability.

EXAMPLES

Next, the present invention will be explained in more detail by way of examples, which are not intended to be limiting of the present invention.

Example 1

As an organic dye, a mixture dye consisting of a cyanine dye NK3721 (manufactured by Hayashibara Biochemical Laboratories, Inc.) and a cyanine dye OM-57 (manufactured by Fuji Photo Film Co., LTD.) in a ratio (by weight) of 6:4 was used.

To 100 g of 2,2,3,3-tetrafluoro-1-propanol (TFP) which had been increased in its purity through distillation to a level in which the content of the high-boiling-point fluorinated alcohol, represented by the general formula (1): $H(CF_2-CF_2)n-CH_2OH$ where n is an integer of 2 to 4, came to 0.001% by weight or less (not more than detection limit) was added 2 g of the above cyanine mixed dye to prepare a dye solution. The dye solution was applied onto a polycarbonate substrate with a diameter of 120 mm and a thickness of 1.2 mm having pregroove, produced by injection molding, by a spin coating method. In the spin coating, the initial rotating speed was set to 300 rpm when the dye solution was dripped on the substrate, gradually increased and finally set to 5000 rpm. After having been dried (at 60° C., for 3 hours), an Ag layer with a thickness of 100 nm was formed on the dye layer by a sputtering method. Further, an ultraviolet-rays curable type acrylic resin DAICURE CLEAR SD318 (manufactured by Dainippon Ink and Chemicals, Inc.) was applied onto the Ag layer by a spin coating method to form a protective layer with a thickness of 5 μm. Thus 10 optical recording media according to the present invention were made. The thickness of the organic dye layer was about 250 nm at the groove portion and about 150 nm at the land portion.

Recordings were made in the resulting optical recording media by using a commercially available CD-R drive and the optical recording media were then subjected to a weatherability test performed in a thermo-hygrostat kept at a temperature of 80° C. and a humidity of 80% for 200 hours. The characteristics (jitter value, block error rate) before and after the weatherability test was measured and evaluated by using a CD-CATS-SA3 manufactured by Audio Development. As shown in Tables 2 and 3, any of the media showed superior initial (before the weatherability test) characteristics as compared with a conventional CD-R, and these characteristics did not deteriorate even after the weatherability test.

Table 2 shows the jitter value before and after the weatherability test. In Table 2, the jitter value is an average value of the measured values of 10 samples, and the measuring position is set at a radius of the center of the medium. Table 3 shows an average value and a maximum value of the block error rates of the measured 10 samples before and after the weatherability test.

The content of the high-boiling-point fluorinated alcohol in TFP was determined by using a gas chromatography (GC14B manufactured by Shimadzu Corporation). The same is true in Comparative Examples.

Comparative Example 1 and 2

The same processes as Example 1 were carried out except that 100 g of TFP, which respectively contained 0.0019% (Comparative Example 1) and 0.0013% (Comparative Example 2) by weight of fluorinated alcohol (2,2,3,3,4,4,5,5-octafluoro-1-pentanol) represented by the general formula (1) where n is a value of 2, was used to obtain 10 samples of optical recording media. These TFP was respectively prepared by adding 2,2,3,3,4,4,5,5-octafluoro-1-pentanol to an ultra-high purity TFP used in Example 1.

The characteristics of the optical recording media were measured and evaluated in the same manner as Example 1, and as shown in Table 2 and Table 3, the results showed that, although no difference was seen from Example 1 with respect to the initial value of the block error rate, the initial value of the jitter was inferior as compared with Example 1, and after the weatherability test, both the block error rate and jitter deteriorated. In particular, the block error rate deteriorated extremely.

Comparative Example 3 and 4

The same processes as Example 1 were carried out except that 100 g of TFP, which respectively contained 0.0018% (Comparative Example 3) and 0.0015% (Comparative Example 4) by weight of fluorinated alcohol (2,2,3,3,4,4,5,5,6,6,7,7-dodecafluoro-1-heptanol) represented by the general formula (1) where n is a value of 3, was used to obtain 10 samples of optical recording media. These TFP was respectively prepared by adding 2,2,3,3,4,4,5,5,6,6,7,7-dodecafluoro-1-heptanol to an ultra-high purity TFP used in Example 1.

The characteristics of the optical recording media were measured and evaluated in the same manner as Example 1, and as shown in Table 2 and Table 3, the results showed that, although difference was seen from Example 1 with respect to the initial value of the block error rate, the initial value of the jitter was inferior as compared with Example 1, and after the weatherability test, both the block error rate and jitter deteriorated. In particular, the block error rate deteriorated extremely.

Comparative Example 5 and 6

The same processes as Example 1 were carried out except that 100 g of TFP, which respectively contained 0.0019% (Comparative Example 5) and 0.0014% (Comparative Example 6) by weight of fluorinated alcohol (2,2,3,3,4,4,5,5,6,6,7,7,8,8,9,9-hexadecafluoro-1-nonanol) represented by the general formula (1) where n is a value of 4, was used to obtain 10 samples of optical recording media. These TFP was respectively prepared by adding 2,2,3,3,4,4,5,5,6,6,7,7,8,8,9,9-hexadecafluoro-1-nonanol to an ultra-high purity TFP used in Example 1.

The characteristics of the optical recording media were measured and evaluated in the same manner as Example 1, and as shown in Table 2 and Table 3, the results showed that, although no difference was seen from Example 1 with respect to the initial value of the block error rate, the initial value of the jitter was inferior as compared with Example 1, and after the weatherability test, both the block error rate and jitter deteriorated. In particular, the block error rate deteriorated extremely.

TABLE 2

Jitter value

| | Measuring position | Example 1 | Comparative Example 1 | Comparative Example 2 | Comparative Example 3 | Comparative Example 4 | Comparative Example 5 | Comparative Example 6 |
|---|---|---|---|---|---|---|---|---|
| Before weatherability test | Radius of 25 mm | 7.36 | 8.03 | 7.99 | 8.47 | 8.25 | 8.61 | 8.45 |
| | Radius of 40 mm | 7.34 | 7.98 | 7.95 | 8.46 | 8.31 | 8.63 | 8.52 |
| | Radius of 55 mm | 7.45 | 8.12 | 8.09 | 8.50 | 8.39 | 8.74 | 8.58 |
| After weatherability test | Radius of 25 mm | 7.87 | 9.05 | 8.98 | 9.71 | 9.43 | 9.98 | 9.86 |
| | Radius of 40 mm | 7.89 | 9.11 | 9.03 | 9.70 | 9.51 | 9.92 | 9.84 |
| | Radius of 55 mm | 7.93 | 9.17 | 9.12 | 9.97 | 9.69 | 10.07 | 9.93 |

TABLE 3

Block error rate

| | Example 1 | Comparative Example 1 | Comparative Example 2 | Comparative Example 3 | Comparative Example 4 | Comparative Example 5 | Comparative Example 6 |
|---|---|---|---|---|---|---|---|
| Before weatherability test | | | | | | | |
| Average value | 1 | 1 | 1 | 1 | 1 | 1 | 1 |
| Maximum value | 11 | 15 | 13 | 12 | 11 | 14 | 13 |
| After weatherability test | | | | | | | |
| Average value | 1 | 1267 | 996 | 886 | 878 | 1827 | 1659 |
| Maximum value | 15 | 1856 | 1629 | 1132 | 1097 | 2259 | 1928 |

What is claimed is:

1. A dye solution for manufacturing an optical recording medium having an organic dye layer and a reflecting layer in this order on a light-transmittable substrate, wherein said dye solution includes a fluorinated alcohol consisting of tetrafluoro-1-propanol and between 0 and 0.001% of a high-boiling-point fluorinated alcohol impurity with a boiling point of not less than 120° C., wherein the high-boiling-point fluorinated alcohol impurity is mainly represented by general formula (1):

$$H(CF_2-CF_2)_n-CH_2OH \quad (1),$$

where n is an integer of 2 to 4.

2. The dye solution for manufacturing an optical recording medium according to claim 1, wherein a molecular weight of the high-boiling-point fluorinated alcohol impurity is 150 to 500.

3. The dye solution for manufacturing an optical recording medium according to claim 1, wherein the high-boiling-point fluorinated alcohol impurity is not detected.

4. The dye solution for manufacturing an optical recording medium according to claim 1, wherein the high-boiling-point fluorinated alcohol impurity is not included.

5. An optical recording medium having an organic dye layer and a reflecting layer in this order on a light-transmittable substrate, wherein an organic dye solution to be used in said organic dye layer is formed by using a solvent containing a fluorinated alcohol consisting of tetrafluoro-1-propanol and between 0 and 0.001% of a high-boiling-point fluorinated alcohol impurity with a boiling point of not less than 120° C., wherein the high-boiling-point fluorinated alcohol impurity is mainly represented by general formula (1):

$$H(CF_2-CF_2)_n-CH_2OH \quad (1),$$

wherein n is an integer of 2 to 4.

6. The optical recording medium according to claim 5, wherein in said fluorinated alcohol, the content of the high-boiling-point fluorinated alcohol impurity with a molecular weight of 150 to 500 is 0.001% by weight or less.

* * * * *